(12) United States Patent
Weiman et al.

(10) Patent No.: US 9,757,151 B2
(45) Date of Patent: Sep. 12, 2017

(54) ENDOSCOPIC FUSION SYSTEM AND METHOD WITH NEUROMONITORING

(71) Applicant: GLOBUS MEDICAL, INC., Audubon, PA (US)

(72) Inventors: Mark Weiman, Coatesvile, PA (US); Kevin Gahman, Douglassville, PA (US); John Henry, Wayne, PA (US)

(73) Assignee: Globus Medical, Inc., Audubon, PA (US)

( * ) Notice: Subject to any disclaimer, the term of this patent is extended or adjusted under 35 U.S.C. 154(b) by 105 days.

(21) Appl. No.: 14/540,071

(22) Filed: Nov. 13, 2014

(65) Prior Publication Data
US 2015/0133733 A1    May 14, 2015

Related U.S. Application Data

(60) Provisional application No. 61/904,297, filed on Nov. 14, 2013.

(51) Int. Cl.
| | |
|---|---|
| *A61B 17/34* | (2006.01) |
| *A61B 1/32* | (2006.01) |
| *A61B 17/70* | (2006.01) |
| *A61B 17/88* | (2006.01) |
| *A61B 17/00* | (2006.01) |
| *A61B 90/00* | (2016.01) |

(52) U.S. Cl.
CPC ............ *A61B 17/3478* (2013.01); *A61B 1/32* (2013.01); *A61B 17/3403* (2013.01); *A61B 17/3417* (2013.01); *A61B 17/3439* (2013.01); *A61B 17/3468* (2013.01); *A61B 17/7061* (2013.01); *A61B 17/8816* (2013.01); *A61B 17/8897* (2013.01); *A61B 2017/00039* (2013.01); *A61B 2017/00261* (2013.01); *A61B 2090/062* (2016.02)

(58) Field of Classification Search
CPC ............ A61B 2017/00261; A61B 2017/00039
See application file for complete search history.

(56) References Cited

U.S. PATENT DOCUMENTS

| | | | | |
|---|---|---|---|---|
| 2010/0114147 | A1* | 5/2010 | Biyani | ...................... A61B 1/32 606/191 |
| 2011/0208226 | A1* | 8/2011 | Fatone | ............... A61B 17/3421 606/191 |
| 2012/0232552 | A1* | 9/2012 | Morgenstern Lopez | ................. A61B 18/1487 606/45 |
| 2014/0172002 | A1* | 6/2014 | Predick | .............. A61B 17/3417 606/191 |
| 2014/0303666 | A1* | 10/2014 | Heiman | ............... A61B 17/025 606/198 |
| 2014/0330083 | A1* | 11/2014 | O'Neil | ............... A61B 17/3439 600/202 |

* cited by examiner

*Primary Examiner* — Jan Christopher Merene (57) ABSTRACT

Systems, methods, and kits for performing endoscopic fusion with neuromonitoring. The endoscopic fusion may be performed, for example, through a cannula providing a portal to the disc space. Throughout various steps in the procedure, neuromonitoring may occur to minimize the possibility of injuring or contacting a nerve.

19 Claims, 10 Drawing Sheets

ENDOSCOPIC FUSION SYSTEM AND METHOD WITH NEUROMONITORING

CROSS-REFERENCE TO RELATED APPLICATIONS

This application claims priority to provisional application No. 61/904,297 filed Nov. 14, 2013, the entire contents of which are incorporated herein by reference in its entirety for all purposes.

FIELD OF THE INVENTION

The present disclosure generally provides a system and method for performing endoscopic fusion procedures while neuromonitoring.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing at least a portion of the spine. This treatment may include a fusion between adjacent vertebrae. There are a number of known conventional fusion devices and methodologies in the art for accomplishing intervertebral fusion. These include screw and rod arrangements, bone implants, and fusion devices which include a cage or other implant mechanism which may be packed with bone and/or bone growth inducing substances, for example. With certain fusion devices, the intervertebral disc may be partially or fully removed. An intervertebral fusion device may then be inserted between neighboring vertebrae to maintain normal disc spacing and restore spinal stability, thereby facilitating an intervertebral fusion and alleviating the associated pain.

The risk of injury to a nerve is a concern when performing surgical procedures in close proximity to the spine or spinal nerves. In particular, minimally invasive surgical procedures with small incisions limit direct visualization of the targeted site. For example, endoscopic procedures may be performed through a cannula or endoscope working channel with a limited amount of access to the surgical site. Surgeons increasingly rely on neuromonitoring techniques to monitor the nerves during such surgeries in order to avoid inadvertently injuring or contacting a nerve. Neuromonitoring functions to determine the integrity of a neural structure or the proximity of a surgical tool or instrument to that neural structure and to minimize contact or trauma to the area. There remains a need for enhanced neuromonitoring tools and techniques especially for use during minimally invasive or endoscopic spinal fusion procedures.

SUMMARY OF THE INVENTION

To meet this and other needs, methods, systems, and kits for performing endoscopic fusion with neuromonitoring are provided. The endoscopic fusion may be performed, for example, through a cannula providing a portal to the disc space. In particular, a spinal procedure including, for example, a discectomy, inserting an implant into the disc space, and/or inserting graft material into the disc space and/or the implant may be performed through the cannula. Throughout various steps in the procedure, neuromonitoring may occur to minimize the possibility of injuring or contacting a nerve. The neuromonitoring may include monitoring for the presence of or damage to sensory nerves and/or motor nerves, for example.

According to one embodiment, a method for performing endoscopic fusion may include the following steps. An access target in a disc space may be determined and an incision created. An assembled needle may be inserted into the disc space through the incision. The assembled needle may include a stylet inserted through an inner lumen of a needle cannula. The needle cannula may be in the form of a c-channel including at least one channel extending along a longitudinal axis of the needle cannula. The needle cannula may be configured to permit the stylet to enter and exit the cannula through the channel. The needle cannula may be partially or fully insulated. The stylet is removed and a k-wire is inserted through the needle cannula and into the disc space. The needle cannula may be removed after the k-wire is in position. One or more dilators may be positioned over the k-wire and into the disc space. For example, a transition dilator and an implant dilator may be used. A working cannula may be positioned over the dilator and into the disc space and subsequently, the dilator may be removed leaving only the working cannula. A spinal procedure may then be performed through the working cannula and within the disc space. The spinal procedure may include, for example, a discectomy, inserting an implant into the disc space, and/or inserting graft material into the disc space and/or the implant.

Throughout various steps in the procedure, neuromonitoring may occur to minimize the possibility of injuring or contacting a nerve. For example, at least one of the needle cannula, the stylet, the k-wire, and the dilator may be stimulated during or after insertion for neuromonitoring. In particular, the dilator may be directionally stimulated as the dilator advances into the disc space. The dilator may be fully or partially insulated. The dilator may include an assembly of an insulated dilator with a probe extending therethrough. For example, the probe may be un-insulated or partially insulated, and the probe may be stimulated during insertion. The dilator may include a channel along a longitudinal axis and the dilator may be configured to permit the probe to enter and exit the dilator through the channel.

According to another embodiment, a method for performing endoscopic fusion may include the following steps: (a) determining an access target in a disc space and creating an incision; (b) inserting an assembled needle into the disc space through the incision, the assembled needle including a stylet inserted through an inner lumen of a needle cannula, wherein the needle cannula is in the form of a c-channel including at least one channel extending along a longitudinal axis of the needle cannula, the needle cannula being configured to permit the stylet to enter and exit the cannula through the channel, and wherein the needle cannula is at least partially insulated; (c) removing the stylet and inserting a k-wire through the needle cannula and into the disc space; (d) removing the needle cannula after the k-wire is in position; (e) positioning a dilator over the k-wire and into the disc space; (f) positioning a working cannula over the dilator and into the disc space; (g) performing a spinal procedure within the disc space, such as a discectomy; (h) inserting a dilator through the working cannula and subsequently, removing the working cannula; (i) inserting an implant cannula over the dilator and subsequently, removing the dilator; and (j) inserting an implant through the implant cannula and positioning the implant within the disc space.

Once the spinal procedure is complete (e.g., implanting the fusion device), the implant cannula may be removed and the incision can be closed.

The implant may include any suitable fusion implants known in the art. In a preferred embodiment, the implant is an expandable implant. An expandable fusion device may be capable of being placed into the disc space down an endoscopic tube and then expanded into an expanded configuration. In particular, the expandable implant may be inserted through the implant cannula in an unexpanded state and, after implantation, the implant may then be expanded to a desired height. If desired, the implant and/or the disc space may be filled with a graft material. In particular, after inserting the implant through the implant cannula and positioning the implant within the disc space, graft material may be packed into the implant and/or the disc space through the implant cannula.

According to another embodiment, a system for endoscopic fusion includes one or more devices, such as a needle, a k-wire, one or more dilators, a working cannula, and the like. In particular, an assembled needle may be configured to be inserted into a disc space. The assembled needle may include a stylet positioned through an inner lumen of a needle cannula. The needle cannula may be in the form of a c-channel including at least one channel extending along a longitudinal axis of the needle cannula. The needle cannula may be configured to permit the stylet to enter and exit the cannula through the channel. The needle cannula may be at least partially insulated. The k-wire may be configured to replace the stylet through the needle cannula. The dilator may be configured to be positioned over the k-wire. The dilator may also include a channel along a longitudinal axis, the dilator being configured to permit the probe to enter and exit the dilator through the channel. The working cannula may be configured to be positioned over the dilator, and the dilator being subsequently removed to provide working access to perform a spinal procedure within the disc space. At least one of the needle cannula, the stylet, the k-wire, and the dilator may be configured to be stimulated for neuromonitoring.

According to yet another embodiment, a kit for endoscopic fusion includes one or more instruments or devices described in this document, such as a needle assembly including a stylet positioned through an inner lumen of a needle cannula, a k-wire, one or more dilators, a working cannula, implant cannula, implants, and the like. One or more of these instruments or devices may be equipped for neuromonitoring including areas that are insulated, un-insulated, partially insulated, fully conductive, partially conductive, and the like. One or more electrodes may form at least a portion of the instrument or device or may be disposed on the instrument or device.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Embodiments of the disclosure are generally directed to methods, systems, and kits for performing endoscopic fusion with neuromonitoring. During a surgical procedure, such as a spinal surgery, as an instrument is advanced towards and into a patient's spine, neuromonitoring may be performed to detect and signal the presence of nerves in the patient's tissue as the instrument is advanced deeper into the body. During such a procedure, one or more instruments or devices may be used, such as a needle assembly including a stylet positioned through an inner lumen of a needle cannula, a k-wire, one or more dilators, probes, a working cannula, implant cannula, implants, and the like.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of."

According to one embodiment, a method for performing endoscopic fusion may include one or more of the following steps. An access target in a disc space may be determined and an incision is created. An assembled needle may be inserted into the disc space through the incision. The assembled needle may include a stylet inserted through an inner lumen of a needle cannula. The needle cannula may be in the form of a c-channel including at least one channel extending along a longitudinal axis of the needle cannula. The needle cannula may be configured to permit the stylet to enter and exit the cannula through the channel. The needle cannula may be partially or fully insulated. The stylet is removed and a k-wire is inserted through the needle cannula and into the disc space. The needle cannula may be removed after the k-wire is in position. One or more dilators may be positioned over the k-wire and into the disc space. For example, a transition dilator and an implant dilator may be used. A working cannula may be positioned over the dilator and into the disc space and subsequently, the dilator may be removed leaving only the working cannula. A spinal procedure may then be performed through the working cannula and within the disc space. The spinal procedure may include, for example, a discectomy, inserting an implant into the disc space, and/or inserting graft material into the disc space and/or the implant. Throughout various steps in the procedure, neuromonitoring may occur to minimize the possibility of injuring or contacting a nerve.

One or more neuromonitoring components may form at least a portion of the instruments or devices or may be disposed on the instruments or devices. The neuromonitoring components may include conductive materials and/or insulative materials as would be known to one of ordinary skill in the art. For example, conductive materials may include conductive wiring, conductive epoxy, conductive ink, conductive filaments, and the like. The insulative materials may be in the form of an insulating layer, coating, or housing and may include any material having low conductivity such that flow of current therethrough is negligible.

The components may also include response sensors (e.g., sensory electrodes) or stimulating electrodes, for example. The electrodes may generally provide neuromonitoring points, assisting in location, proximity, pathology, and direction of nerve tissue. Response sensors sense nerve responses from nerves in the proximity of the instrument when those nerves are stimulated by stimulus signals delivered elsewhere, for example to sensory tissue. The response sensors detect electrical signals in the vicinity of the instrument. The sensors may detect changes in the body's electrical potential in tissue surrounding the instrument, for example, when a nerve in the vicinity of the instrument is stimulated and depolarizes. The depolarization of the nerve caused by a propagating nerve signal, or action potential, and subsequent repolarization of the nerve may be detected by the response sensor. Stimulating electrodes deliver electrical signals to stimulate nerves in the proximity of the instrument, for example, when the system is used to monitor both sensory and motor nerves.

The neuromonitoring procedures may include monitoring for the presence of or damage to sensory nerves and/or motor nerves. In some systems, including systems that monitor for both sensory and motor nerves, components of the monitoring systems (e.g., stimulating electrodes and response sensors), may be combined with one or more surgical instruments.

During neuromonitoring, stimulations delivered to nerve responses may be controlled and processed by a neuromonitor, for example. The neuromonitor may include a programmable processor-based device that includes processing circuitry for controlling the neuromonitor and/or the surgical system. The neuromonitor may include stimulation processing circuitry that controls the stimulation sources (e.g., by controlling the amplitude, duration, or frequency of stimulation signals). The neuromonitoring system may include hardware and/or software platforms known to those of ordinary skill in the art that control, send, receive, and process the stimulation signals, detected responses, and other communications during the neuromonitoring process. The neuromonitor may also receive user input, for example, from a surgeon configuring the system, to control or change one or more of the functions carried out by the system. Any suitable devices, components, systems or configuration known in the art for neuromonitoring may be employed with the instruments and devices described in this document.

Figure 1:
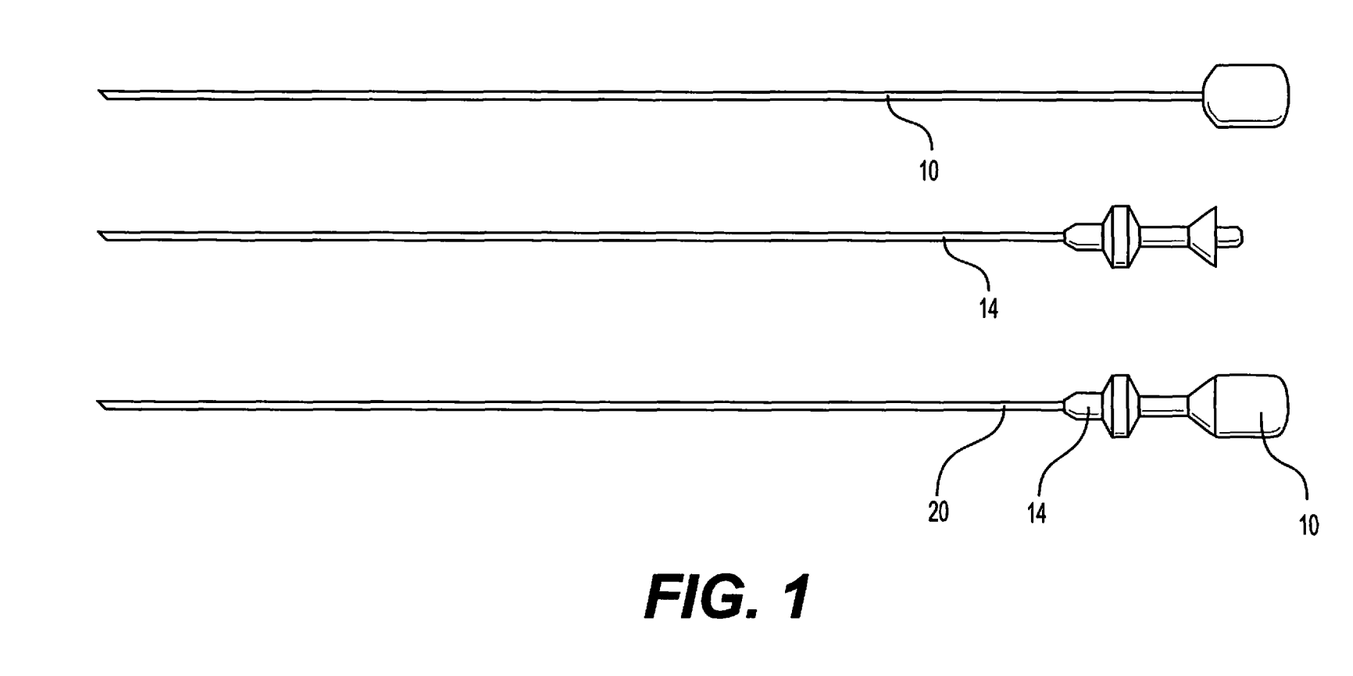
FIG. 1 depicts a stylet, a needle cannula, and a needle assembly with the stylet and needle cannula combined according to one embodiment.
Figure 2:
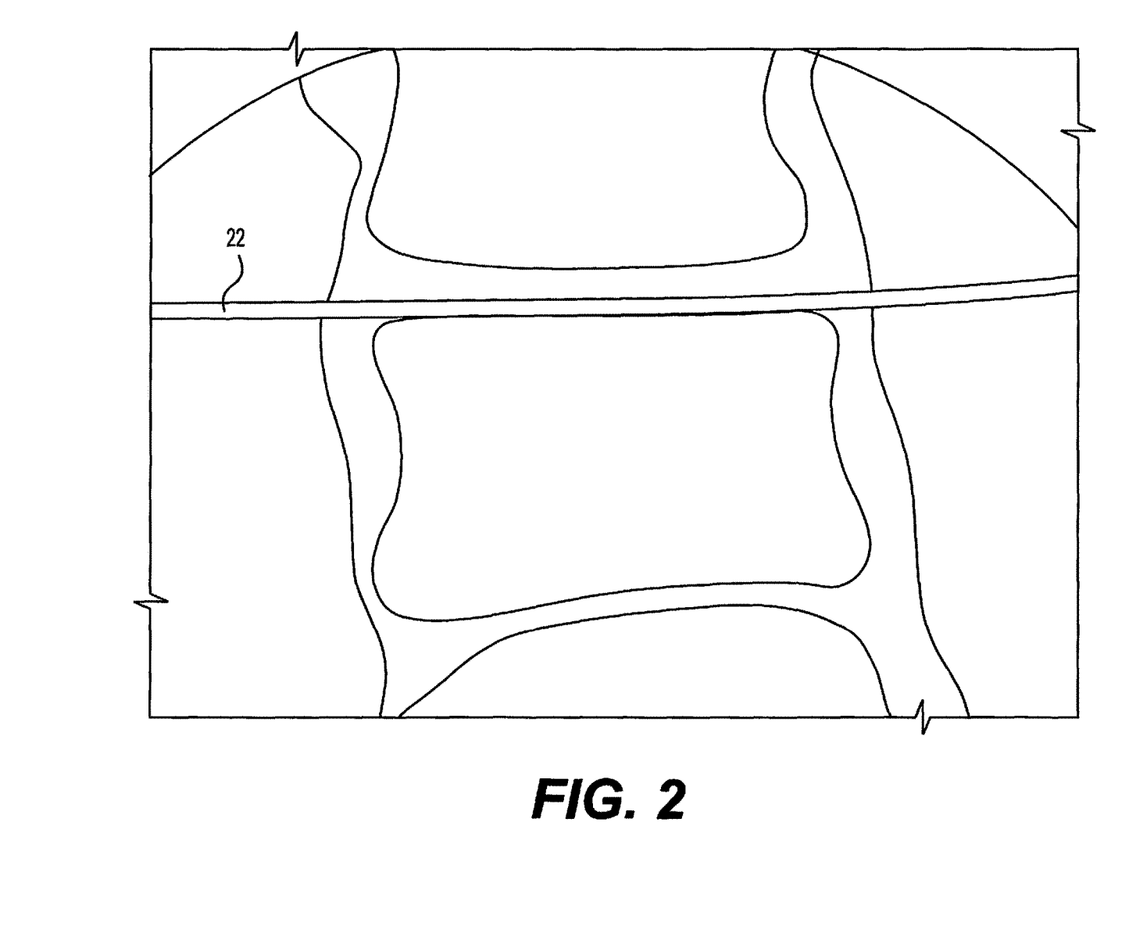
FIG. 2 is a fluoroscopy image of a portion of the spine with a marking instrument to determine a target location.
Figure 3:
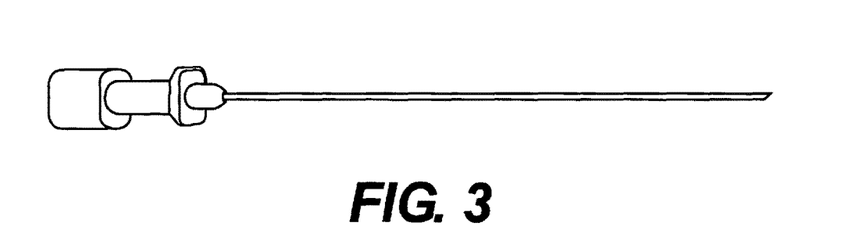
FIG. 3 is an alternative version of a stylet.

With reference to the drawing, FIGS. 1-12 illustrate instruments, devices, and techniques suitable for performing endoscopic fusion with neuromonitoring. FIG. 1 provides a stylet 10 and a needle cannula 14, which may be assembled to form a needle assembly 20. The needle or stylet 10 may be in the form of an elongated body and may include a handle portion at one end. FIG. 3 depicts an alternative type of stylet that may be positioned inside the needle cannula 14 and is capable of being stimulated. The needle cannula 14 may also have an elongated body with a handle portion, which is cannulated with an opening extending centrally along its longitudinal axis from a first opening at a first end to a second opening at a second end of the cannula 14.

When assembled, the stylet 10 is inserted through the inner lumen of the needle cannula 14, thereby providing an assembled needle 20. The needle assembly 20 can be electrically connected to a nerve monitoring system, for example, via a lead (not shown). The stylet 10 may be positioned internally within the needle cannula 14, and the stylet 10 may distally project from the cannula 14. The distally projecting portion of the stylet 10 may include a tip portion that can be used for piercing skin, soft or hard tissues, and applying an electrostimulus to a neural structure. Alternatively, the cannula 14 can be used for neuromonitoring. A portion of the stylet 10 or the entire stylet 10 may be insulated, un-insulated, partially insulated, fully conductive, partially conductive, and the like. Similarly, a portion of the needle cannula 14 or the entire cannula 14 may be insulated, un-insulated, partially insulated, fully conductive, partially conductive, and the like. In a preferred embodiment, the stylet 10 may be partially insulated and the cannula 14 may be fully insulated along its length.

Figure 10:
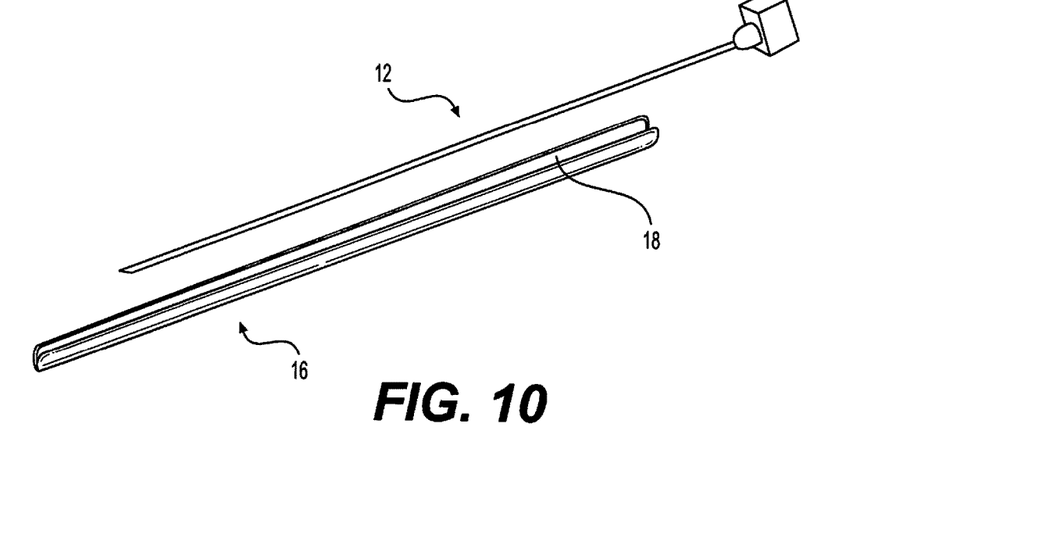
FIG. 10 depicts a needle and a c-channel needle cannula according to one embodiment.

Similar to the stylet 10 and needle cannula 14 shown in FIG. 1, FIG. 10 depicts an alternative version of a stylet 12 and needle cannula 16. Similar to stylet 10, the needle or stylet 12 may be in the form of an elongated body and may include a handle portion at one end and a sharp tip at the other end. The needle cannula 16 may also have an elongated body with a handle portion (not shown). Needle cannula 16 is also cannulated with an opening extending centrally along its longitudinal axis and extending from a first opening at a first end to a second opening at a second end of the cannula 16, but further includes a longitudinal channel 18 in fluid communication with the central opening. The channel 18 includes a longitudinal opening to the exterior of the cannula 16. Thus, the channel 18 provides for a generally c-shaped or u-shaped body for the needle cannula 16. This permits access to the cannulated opening transverse to the longitudinal axis and allows a portion of the stylet 12 or the entire body of the stylet 12 to drop in and out of the needle cannula 16. Any portion of the stylet 12 and/or the needle cannula 16 may be insulated, un-insulated, partially insulated, fully conductive, partially conductive, or the like. In a preferred embodiment, the stylet 12 may be partially insulated and the cannula 16 may be fully insulated along its entire length.

One or more of the following procedural steps may be utilized to perform an endoscopic fusion procedure while neuromonitoring.

1. A radiopaque instrument, marking pen, and/or fluoroscopy may be used to determine an access target. FIG. 2 depicts a radiopaque marker 22 used while taking an x-ray or fluoroscopy image to determine a given location or trajectory to a disc space between two adjacent vertebrae.

2. A needle assembly, for example, as provided in FIG. 1 or 10 described above, including needle cannula 14, 16 with stylet 10, 12 may be positioned into the disc space. As shown in FIG. 1, a neuromonitoring capable and completely insulated needle cannula 14 with stylet 10 may be positioned into the disc space or may stop at any point along the trajectory, for example, from a posterolateral or extraforminal approach (approximately 45 degrees) through Kambin's triangle. The needle cannula 14 and/or the stylet 10 may be stimulated during or after insertion for neuromonitoring.

In one variation shown in FIG. 10, a partially insulated needle cannula 16 with stylet 12 in inserted into the disc space. The needle cannula 16 is configured to be simulated during insertion. In an alternative configuration, the insulated stylet 12 is inserted into the insulated c-channel needle cannula 16. In this variation, the stylet 12 would be stimulated during the insertion process. It should be noted that the c-channel needle cannula 12 can also be fully or partially insulated thereby enabling the c-channel needle cannula 16 to be also stimulated for neuromonitoring purposes during the insertion process.

Figure 12:
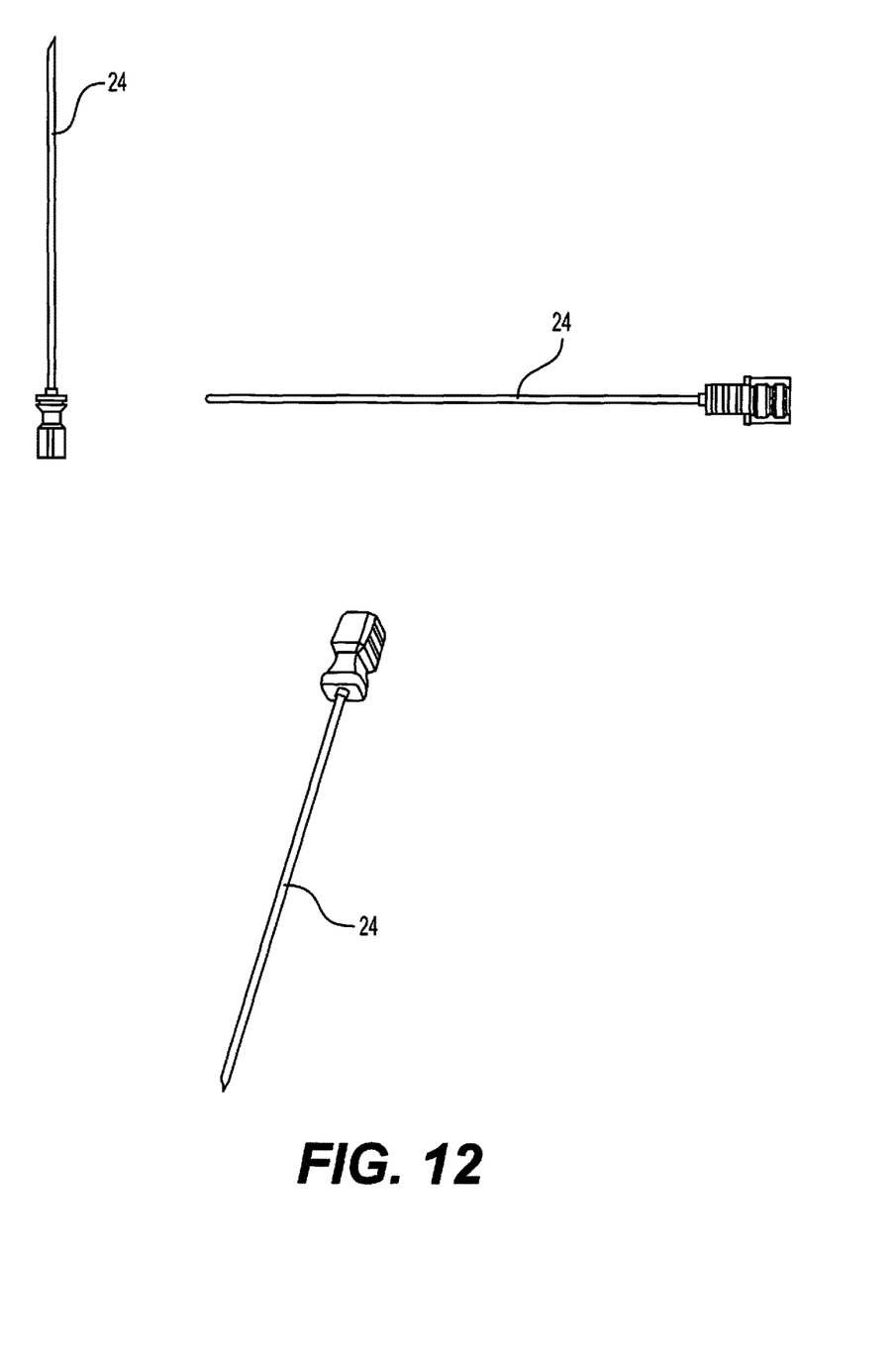
FIG. 12 depicts alternative views of an example of a PEEK sleeve.

In another variation, before insertion, the needle 10, 12 and cannula 14, 16 is positioned through a cannulated PEEK sleeve 24 which allows for a small portion of the needle 10, 12 to protrude from the distal end of the sleeve 24. The assembly of the needle 10, 12, cannula 14, 16, and the PEEK sleeve 24 is then inserted into the disc space and the needle 10, 12 is stimulated with a gator clip or similar device. Stimulation may be performed at any point along the entire trajectory and the assembly may be stopped at any point along the trajectory from the skin to the disc space. Although described with respect to a PEEK (polyether ether ketone) sleeve, any suitable polymer sleeve or insulated sleeve may be selected by one of ordinary skill in the art.

Figure 4:
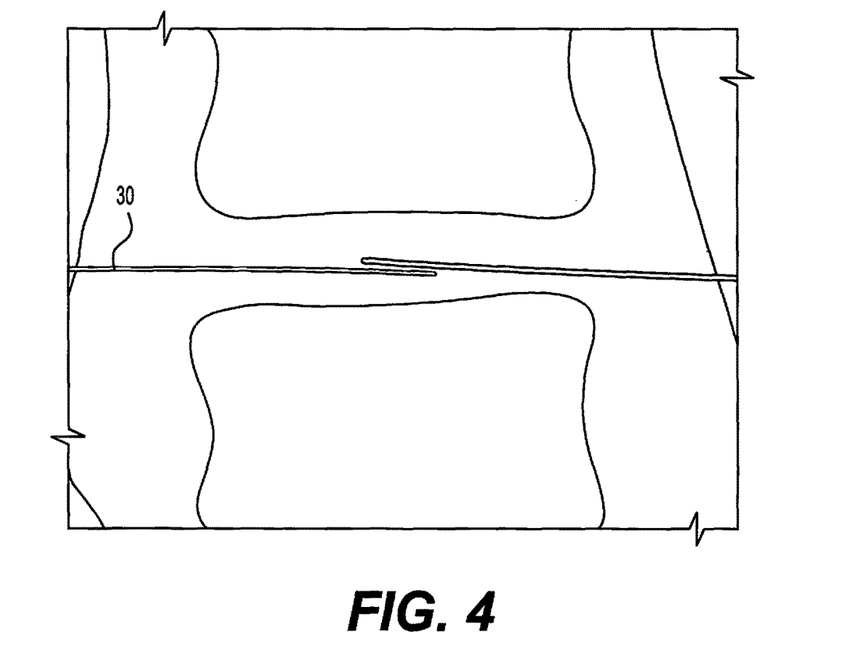
FIG. 4 is a fluoroscopy image of a portion of the spine with k-wires positioned within the disc space.

3. Once inserted, the needle or stylet 10, 12 may be removed and a k-wire 30 may be positioned through the needle cannula 14, 16 into the disc space, or stopped at any point along the trajectory. The k-wire 30 may be stimulated during or after insertion for neuromonitoring. Then, the needle cannula 14, 16 may be removed after the k-wire 30 is positioned within the disc space. FIG. 4 depicts k-wire 30 remaining in the disc space in a fluoroscopy image.

In the embodiment where the needle 10, 12 and cannula 14, 16 is positioned through the cannulated PEEK sleeve 24, the needle 10, 12 can be removed while leaving the PEEK sleeve 24 and needle cannula 14, 16 in situ. The k-wire 30 is then positioned down the needle cannula 14, 16 inside the PEEK sleeve 24. The k-wire 30 is then stimulated during insertion at any point along the trajectory and may stop at any point along the trajectory from the skin to the disc space. The PEEK sleeve 24 is then removed when the desired position of the k-wire 30 is achieved.

Figure 5:
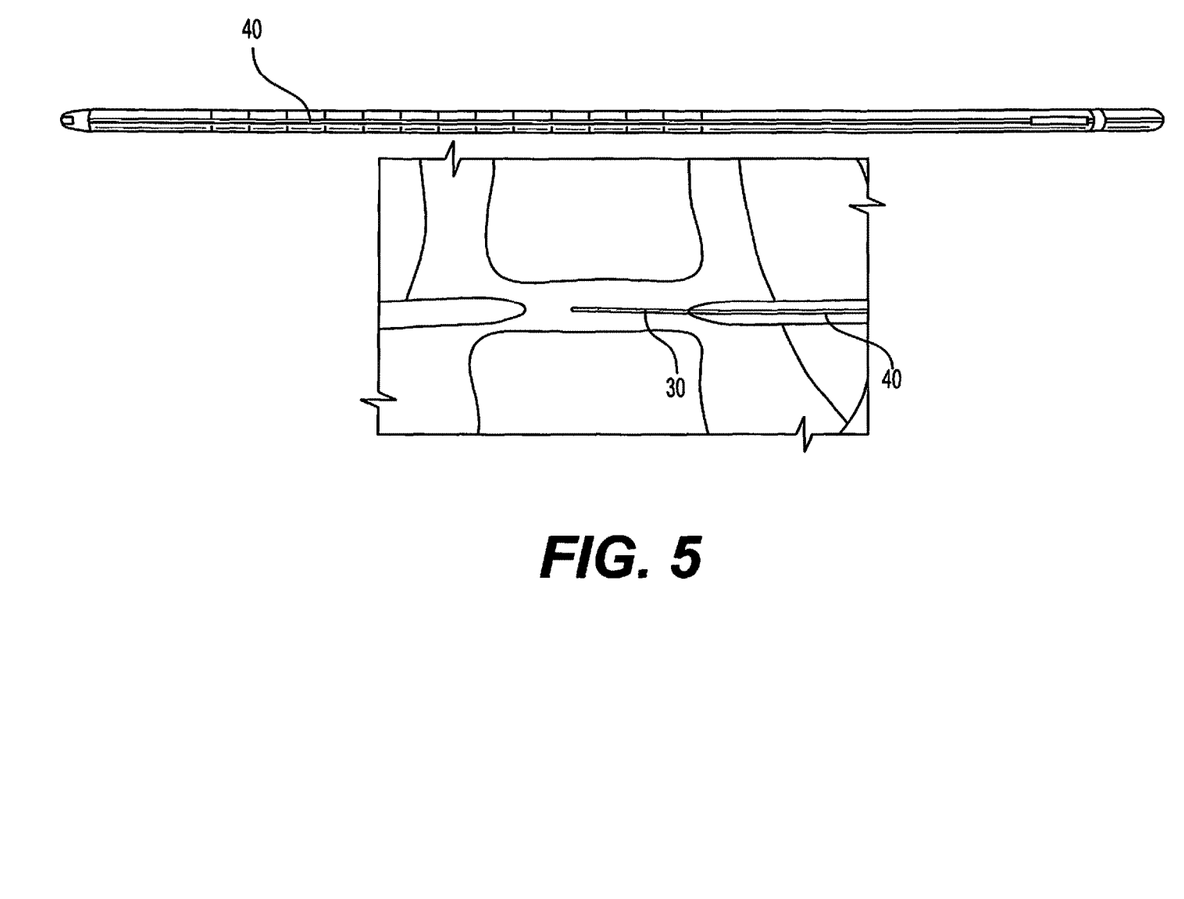
FIG. 5 provides an example of a dilator and a fluoroscopy image of the dilator positioned over the k-wire and advancing into the disc space.

4. At least one dilator 40 may be positioned into the disc space. The dilator 40 may have an elongated body with a tapered distal tip. The body of the dilator 40 is cannulated with an opening extending centrally along its longitudinal axis from a first opening at a first end to a second opening at a second end of the dilator 40. The dilator 40 may be insulated, un-insulated, partially insulated, fully conductive, partially conductive, or the like. In particular, a neuromonitoring capable, all-in one insulated dilator 40 may be positioned over the k-wire 30 and the dilator 40 may be advanced into the disc space. The dilator 40 may be directionally stimulated as the dilator 40 advances into the disc space. FIG. 5 depicts the dilator 40 advancing over the k-wire 30 in a fluoroscopy image.

Figure 11:
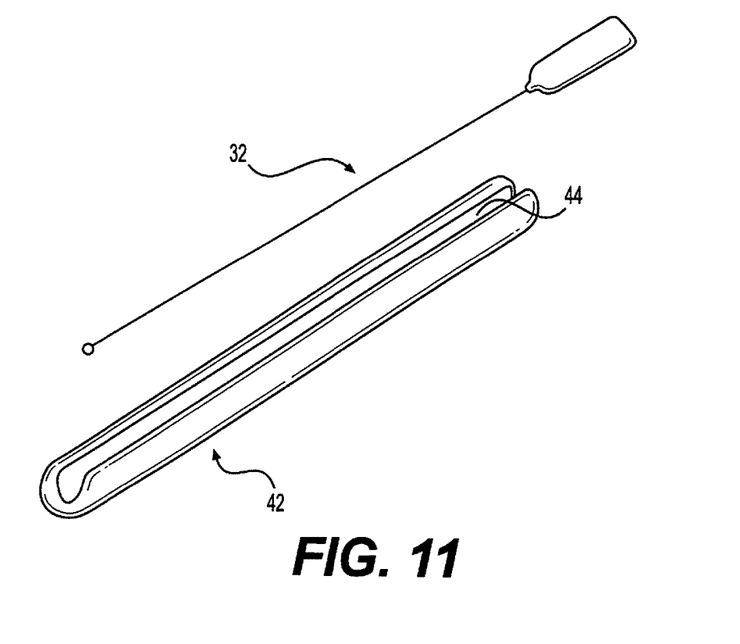
FIG. 11 shows a probe and c-channel dilator according to another embodiment.

In one variation shown in FIG. 11, a completely insulated dilator 42 with an un-insulated probe 32 or a partially insulated probe 32 can be positioned into the disc space as one assembly. The dilator 42 may include a channel 44 positioned along a longitudinal axis, and the dilator 42 may be configured to permit the probe 32 to enter and exit the dilator 42 through the channel 44. The dilator 42 may have an elongated body with an opening extending centrally along its longitudinal axis and extending from a first opening at a first end to a second opening at a second end of the dilator 42 with the longitudinal channel 44 in fluid communication with the central opening. The channel 44 includes a longitudinal opening to the exterior of the dilator 42. Thus, the dilator 42 may provide for a generally c-shaped or u-shaped body for the probe 32 to rest within. This permits access to the cannulated opening transverse to the longitudinal axis and allows a portion of the probe 32 or the entire body of the probe 32 to drop in and out of the dilator 42. In this embodiment, the probe 32 inside the dilator 42 may be stimulated during insertion. In particular, the dilator 42 may be directionally stimulated as the dilator 42 advances into the disc space. The dilator 42 may be fully or partially insulated. The dilator 42 may include an assembly of an insulated dilator 42 with the probe 32 extending therethrough. The probe 32 may be un-insulated or partially insulated, and the probe 32 may be stimulated during insertion.

Figure 6:
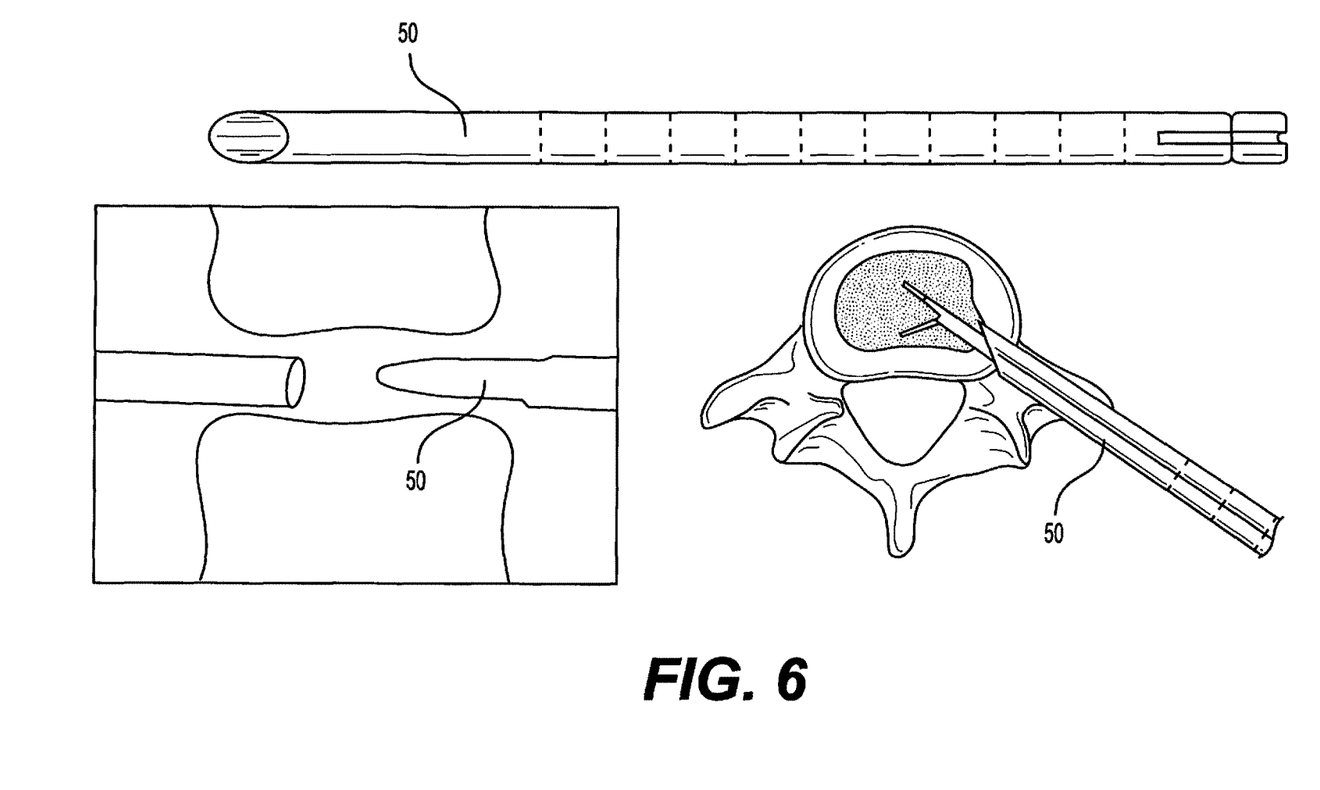
FIG. 6 provides an example of a working cannula, a fluoroscopy image of the working cannula positioned over the dilator, and an axial view of a vertebra with the working cannula positioned in the disc space.

5. A working cannula 50 may then be positioned over the dilator 40, 42 and into the disc space. The working cannula 50 may have an elongated body with a beveled distal tip. The body of the working cannula 50 is cannulated with an opening extending centrally along its longitudinal axis from a first opening at a first end to a second opening at a second end of the working cannula 50. The cannula 50 may be provided with band markings to indicate the depth of the cannula 50 within the disc space, for example. The working cannula 50 may be insulated, un-insulated, partially insulated, fully conductive, partially conductive, or the like. The working cannula 50 may be stimulated during or after insertion for neuromonitoring. FIG. 6 depicts one type of working cannula 50, a fluoroscopy image of the working cannula 50 advancing into the disc space, and an axial view of the working cannula 50 entering the disc space.

Figure 7:
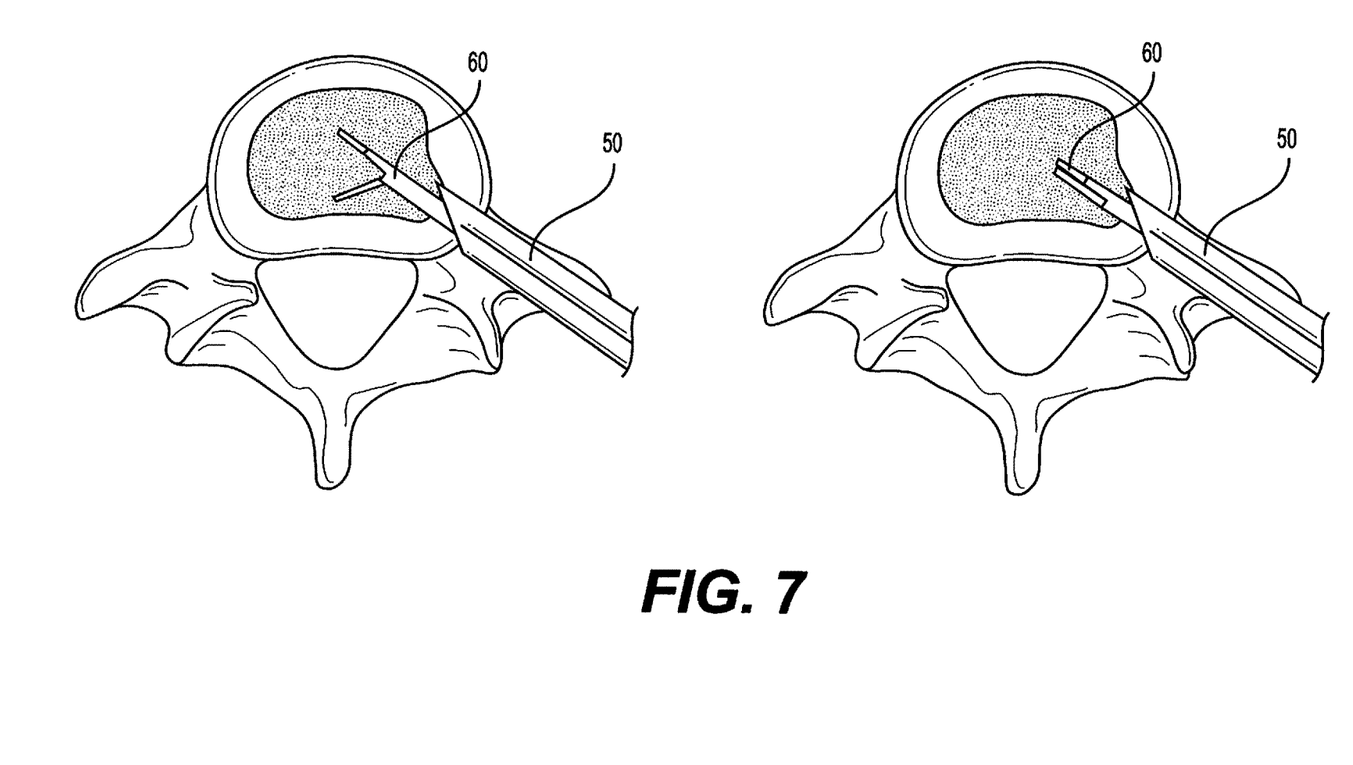
FIG. 7 shows axial views of a vertebra with a discectomy instrument traversing the working cannula, the discectomy instrument including rongeurs in an opened and closed position, respectively.

6. A spinal procedure may be performed within the disc space through the working cannula 50. For example, as shown in the axial views in FIG. 7, a discectomy using a discectomy instrument 60 may be used to remove a portion of the entire disc. In particular, FIG. 7 shows axial views of a vertebra with a discectomy instrument traversing the working cannula, the discectomy instrument including rongeurs in an opened and closed position, respectively.

Pieces of the disc may be removed through suction, forceps, rongeurs, or other similar instruments.

7. Optionally, graft material may be positioned into the disc space by inserting graft material through the working cannula 50. The bone graft materials may include, but are not limited to, demineralized bone matrix (DBM), autograft bone, allograft cortical bone, allograft cancellous bone, synthetic bone grafts, cellular materials, growth factors, and the like.

Figure 8:
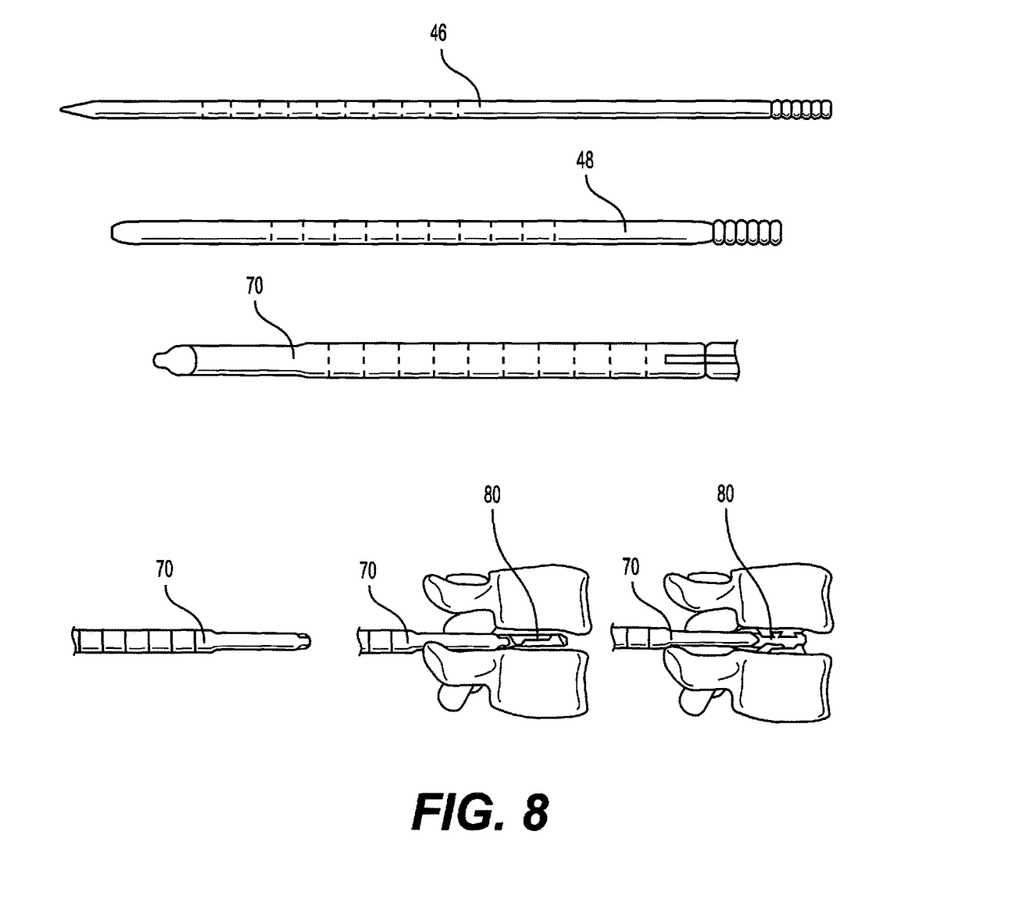
FIG. 8 provides examples of a transition dilator, an implant dilator, an implant cannula, insertion of the implant cannula into the disc space, and deployment of an expandable implant within the disc space from an unexpanded position to an expanded position.

8. A transition dilator 46 may be inserted through the working cannula 50 and then the working cannula 50 may be removed. The transition dilator 46 may have an elongated body with a tapered distal tip. The transition dilator 46 is cannulated with an opening extending centrally along its longitudinal axis from a first opening at a first end to a second opening at a second end of the transition dilator 46. The transition dilator 46 may be insulated, un-insulated, partially insulated, fully conductive, partially conductive, or the like. The transition dilator 46 may be stimulated during or after insertion for neuromonitoring. An example of a transition dilator 46 is shown in FIG. 8.

9. An implant dilator 48 may be inserted over the transition dilator 46 and the transition dilator 46 may be subsequently removed. The implant dilator 48 may have a cannulated, elongated body with an opening extending centrally along its longitudinal axis from a first opening at a first end to a second opening at a second end of the implant dilator 48. The implant dilator 48 may be insulated, un-insulated, partially insulated, fully conductive, partially conductive, or the like. The implant dilator 48 may be stimulated during or after insertion for neuromonitoring. An example of an implant dilator 48 is shown in FIG. 8.

10. An implant cannula 70 may be inserted over the implant dilator 48 and the implant dilator 48 may be subsequently removed. The implant cannula 70 may have a cannulated, elongated body with an opening extending centrally along its longitudinal axis from a first opening at a first end to a second opening at a second end of the implant cannula 70. The implant cannula 70 may be insulated, un-insulated, partially insulated, fully conductive, partially conductive, or the like. The implant cannula 70 may be stimulated during or after insertion for neuromonitoring. An example of an implant cannula 70 is also shown in FIG. 8. FIG. 8 also depicts a lateral view of the implant cannula 70 being inserted into the disc space.

11. After the implant cannula 70 is in position, an implant 80 may be inserted through the implant cannula 70 and positioned within the disc space. In one preferred embodiment, an expandable implant 80 is inserted through the implant cannula 70. In particular, the expandable implant 80 may be inserted through the implant cannula 70 in an unexpanded state and, after implantation, the implant 80 may then be expanded to a desired height. The implant 80 may include any suitable fusion implants known in the art. For example, suitable expandable implants are described in U.S. Pat. Nos. 8,062,375; 8,282,683; 8,398,713; 8,435,298; 8,491,659; 8491659; 8,632,595; 8,845,731; 8,845,732; and 8,845,734, all of which are incorporated herein by reference in their entireties for all purposes.

As shown in FIG. 8, the expandable implant 80 is positioned within the disc space in an unexpanded state. After the expandable implant 80 has been inserted into the appropriate position in the intervertebral disc space, the expandable implant 80 can then be expanded into the expanded position. In the event the expandable implant 80 needs to be repositioned or revised after being installed and expanded, the expandable implant 80 can be contracted back to the unexpanded configuration, repositioned, and expanded again once the desired positioning is achieved.

Although the preceding discussion only discussed having a single implant 80 implanted in the intervertebral space, it is contemplated that more than one implant 80 can be inserted in the intervertebral space. It is further contemplated that each implant 80 does not have to be finally installed in the fully expanded state. Rather, depending on the location of the implant 80 in the intervertebral disc space, the height of the implant 80 may vary from unexpanded to fully expanded. It should be noted that, as well as the height being varied from an unexpanded state to an expanded state, the implant 80 may be positioned permanently anywhere between the expanded state and the unexpanded state.

Figure 9:
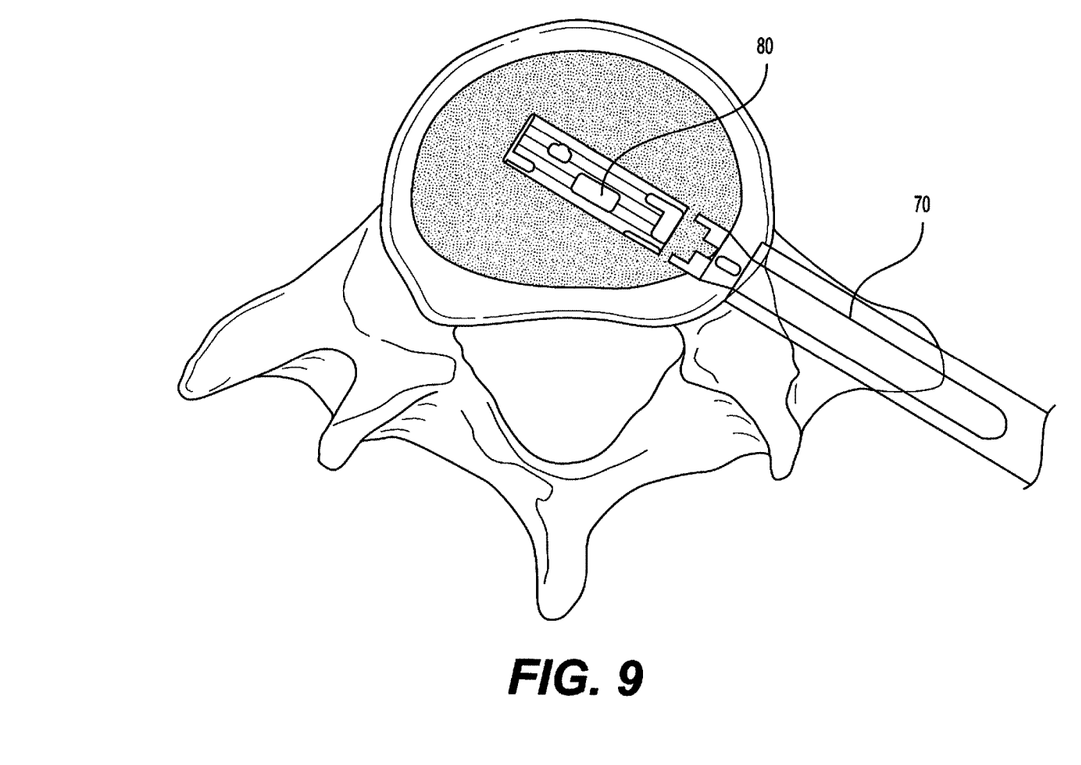
FIG. 9 depicts an axial view of the expandable implant positioned within the disc space and packed with graft material.

12. Optionally, graft material may be packed into the disc space and/or the implant 80 through the implant cannula 70. The bone graft materials may include, but are not limited to, demineralized bone matrix (DBM), autograft bone, allograft cortical bone, allograft cancellous bone, synthetic bone grafts, cellular materials, growth factors, and the like. FIG. 9 depicts implant 80 positioned within the disc space with bone graft material packed in and around the implant 80.

13. After the implant 80 is positioned, the implant cannula 70 may be removed and the open incision may be closed (e.g., via stitching or the like).

The above steps are provided as guidelines, it should be noted that variations may be utilized. Throughout various steps in the procedure, neuromonitoring may occur to minimize the possibility of injuring or contacting a nerve. In particular, any of the instruments or devices used can be insulated with directional neuromonitoring capabilities. For example, at least one of the needle cannula, the stylet, the k-wire, and the dilator may be stimulated during or after insertion for neuromonitoring.

The devices and instruments described herein may be provided in systems and kits for endoscopic fusion. In particular, such systems or kits may include one or more instruments or devices, such as needles, k-wires, dilators, probes, cannulas, implants, and the like. One of more of these instruments or devices may be equipped for neuromonitoring including areas that are insulated, un-insulated, partially insulated, fully conductive, partially conductive, and the like. One or more electrodes may form at least a portion of the instrument or device or may be disposed on the instrument or device.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A method for performing endoscopic fusion, comprising:
   determining an access target in a disc space and creating an incision;
   inserting an assembled needle into the disc space through the incision, the assembled needle including a stylet inserted through an inner lumen extending centrally along a longitudinal axis of a needle cannula, wherein the needle cannula is in the form of a c-channel including at least one channel extending along the longitudinal axis of the needle cannula, the needle cannula being configured and dimensioned to permit the entire stylet to enter and exit the cannula through the channel in a direction transverse to the longitudinal axis, and wherein the needle cannula is at least partially insulated;

removing the stylet and inserting a k-wire through the needle cannula and into the disc space;

removing the needle cannula after the k-wire is in position;

positioning a dilator over the k-wire and into the disc space;

positioning a working cannula over the dilator and into the disc space and subsequently, removing the dilator; and performing a spinal procedure within the disc space.

2. The method of claim 1, wherein at least one of the needle cannula, the stylet, the k-wire, and the dilator is stimulated during insertion for neuromonitoring.

3. The method of claim 1, wherein the dilator is directionally stimulated as the dilator advances into the disc space.

4. The method of claim 1, wherein the dilator is insulated.

5. The method of claim 1, wherein the dilator includes an assembly of an insulated dilator with a probe extending therethrough, and the assembly is positioned into the disc space.

6. The method of claim 5, wherein the probe is un-insulated or partially insulated, and the probe is stimulated during insertion.

7. The method of claim 5, wherein the dilator includes a channel along a longitudinal axis, the dilator being configured to permit the probe to enter and exit the dilator through the channel.

8. The method of claim 1, wherein inserting the dilator includes inserting a transition dilator; subsequently, inserting an implant dilator over the transition dilator; and subsequently, removing the transition dilator.

9. The method of claim 1, wherein the spinal procedure includes at least one of discectomy, inserting graft material into the disc space, and inserting an implant into the disc space.

10. A method for performing endoscopic fusion, comprising:

determining an access target in a disc space and creating an incision;

inserting an assembled needle into the disc space through the incision, the assembled needle including a stylet inserted through an inner lumen extending centrally along a longitudinal axis of a needle cannula, wherein the needle cannula is in the form of a c-channel including at least one channel extending along the longitudinal axis of the needle cannula, the needle cannula being configured and dimensioned to permit the entire stylet to enter and exit the cannula through the channel in a direction transverse to the longitudinal axis, and wherein the needle cannula is at least partially insulated;

removing the stylet and inserting a k-wire through the needle cannula and into the disc space;

removing the needle cannula after the k-wire is in position;

positioning a dilator over the k-wire and into the disc space;

positioning a working cannula over the dilator and into the disc space;

performing a spinal procedure within the disc space; inserting a dilator through the working cannula and subsequently, removing the working cannula; inserting an implant cannula over the dilator and subsequently, removing the dilator; and inserting an implant through the implant cannula and positioning the implant within the disc space.

11. The method of claim 10, wherein the implant is an expandable implant, and the expandable implant is inserted through the implant cannula in an unexpanded state and, after implantation, the implant is expanded to a desired height.

12. The method of claim 10 further comprising, after inserting the implant through the implant cannula and positioning the implant within the disc space, packing graft material into the disc space through the implant cannula.

13. The method of claim 10 further comprising, after inserting the implant through the implant cannula and positioning the implant within the disc space, removing the implant cannula and closing the incision.

14. A system for endoscopic fusion, comprising:

an assembled needle configured to be inserted into a disc space, the assembled needle including a stylet positioned through an inner lumen extending centrally along a longitudinal axis of a needle cannula, wherein the needle cannula is in the form of a c-channel including at least one channel extending along the longitudinal axis of the needle cannula, the needle cannula being configured and dimensioned to permit the entire stylet to enter and exit the cannula through the channel in a direction transverse to the longitudinal axis, and wherein the needle cannula is at least partially insulated;

a k-wire configured to replace the stylet through the needle cannula;

a dilator configured to be positioned over the k-wire; and a working cannula configured to be positioned over the dilator and the dilator being subsequently removed to provide working access to perform a spinal procedure within the disc space.

15. The system of claim 14, wherein at least one of the needle cannula, the stylet, the k-wire, and the dilator is configured to be stimulated for neuromonitoring.

16. The system of claim 14, wherein the dilator includes an assembly of an insulated dilator with a probe extending therethrough.

17. The system of claim 16, wherein the probe is un-insulated or partially insulated, and the probe is configured to be stimulated for neuromonitoring.

18. The system of claim 16, wherein the dilator includes a channel along a longitudinal axis, the dilator being configured to permit the probe to enter and exit the dilator through the channel.

19. The system of claim 16, wherein the channel is in fluid communication with the inner lumen of the needle cannula.

* * * * *